US006255331B1

(12) United States Patent
El A'mma et al.

(10) Patent No.: US 6,255,331 B1
(45) Date of Patent: Jul. 3, 2001

(54) STABLE BIOCIDAL COMPOSITIONS

(75) Inventors: Beverly Jean El A'mma, Perkiomenville; Susan Lynn Nagahashi, Warminster, both of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/639,781

(22) Filed: Aug. 16, 2000

Related U.S. Application Data

(60) Provisional application No. 60/153,778, filed on Sep. 14, 1999.

(51) Int. Cl.[7] .......................... A01N 43/80; A01N 43/50; A01N 35/02; A01N 25/22; A01N 55/02

(52) U.S. Cl. .......................... 514/372; 514/373; 514/385; 514/386; 514/387; 514/389; 514/390; 514/391; 514/392; 514/393; 514/394; 514/395; 514/396; 514/397; 514/398; 514/399; 514/400; 514/401; 514/499; 514/500; 514/694; 514/697; 514/698; 514/970; 514/971; 514/973; 424/630; 424/631; 424/632; 424/633; 424/634; 424/635; 424/637

(58) Field of Search ...................................... 514/372, 373, 514/385–387, 389–401, 499, 500, 694, 697, 698, 970, 971, 973; 424/630–635, 637–638; 504/151, 152, 156; 422/28

(56) References Cited

U.S. PATENT DOCUMENTS

| | | | |
|---|---|---|---|
| 3,870,795 | * 3/1975 | Miller et al. | 514/372 |
| 4,067,878 | * 1/1978 | Miller et al. | 548/213 |
| 5,037,843 | 8/1991 | Schoenberg | 514/389 |
| 5,041,457 | 8/1991 | Hsu | 514/372 |
| 5,108,500 | * 4/1992 | Mattox | 106/18.33 |
| 5,142,058 | * 8/1992 | Willingham et al. | 548/213 |
| 5,153,213 | * 10/1992 | Schmidt | 514/372 |
| 5,160,527 | * 11/1992 | Law et al. | 514/372 |
| 5,312,827 | 5/1994 | Bayer et al. | 514/372 |
| 5,461,150 | 10/1995 | Gironda et al. | 548/213 |
| 5,464,850 | 11/1995 | Voo et al. | 514/372 |
| 5,668,083 | * 9/1997 | Matsumoto | 504/138 |
| 5,725,806 | * 3/1998 | Ghosh | 548/213 |
| 5,869,510 | * 2/1999 | Mattox | 514/372 |
| 5,910,503 | * 6/1999 | Mattox et al. | 514/372 |
| 5,922,745 | * 7/1999 | McCarthy et al. | 514/372 |
| 5,955,486 | * 9/1999 | Mattox | 514/372 |
| 6,114,366 | * 9/2000 | Lutz et al. | 514/372 |
| 6,121,302 | 9/2000 | Rothenburger et al. | 514/372 |
| 6,153,633 | * 11/2000 | Ghosh et al. | 514/372 |

FOREIGN PATENT DOCUMENTS

| | | |
|---|---|---|
| 3508928 | * 9/1986 | (DE) . |
| 0435439A2 | 7/1991 | (EP) . |
| 880892 | * 12/1998 | (EP) . |
| WO 98/36049 | 8/1998 | (WO) . |

OTHER PUBLICATIONS

Derwent Abstract 1999–208995, 1999.*
Chemical Abstracts 130:248350, 1999.*
Chemical Abstracts 94:96957, 1981.*
Chemical Abstracts 108:11004, 1988.*

* cited by examiner

*Primary Examiner*—John Pak
(74) *Attorney, Agent, or Firm*—Kenneth Crimaldi

(57) ABSTRACT

Disclosed are biocidal compositions comprising mixtures of formaldehyde-releasing imidazolidines, such as 1,3-dimethylol-5,3-dimethylhydantoin, and 3-isothiazolones stabilized with low levels of copper salts.

10 Claims, No Drawings

STABLE BIOCIDAL COMPOSITIONS

This application claims the benefit of U.S. Provisional Application No. 60/153,778, filed on Sep. 14, 1999.

BACKGROUND OF THE INVENTION

The present invention relates to stable biocidtal compositions containing combinations of certain imidazole iodines and 3-isothiazolones. The present invention also relates to the use of low concentrations of copper salts to stabilize such compositions.

Microbicides are used commercially to prevent the growth of microbes in a variety of loci, such as cooling towers, metal working fluid systems, paints and cosmetics. One of the more important classes of microbicides is 3-isothiazolones. Many 3-isothiazolonies have achieved commercial success because they are very effective in preventing microbial growth under a wide variety of conditions and in a variety of loci. Among the most important 3-isothiazolones are 5-chloro--methyl-3-isothiazolone ("CMI"), 2-methyl-3-isothiazolone ("MI"), and mixtures thereof.

Although 3-isothiazolones are highly effective microbicides, some suffer from being unstable under certain conditions. Without the presence of a stabilizer, many 3-isothiazolones chemically degrade and lose microbicidal efficacy. Much research has been devoted to stabilizing 3-isothiazolones. A variety of stabilizers for 3-isothiazolone solutions are known and are described, for example, in U.S. Pat. No. 5,461,150 (Gironda et al) and U.S. Pat. No. 5,312,827 (Bayer et al).

Imidazolidines (which include hydantoins) are another class of Microbicides, and have been used for years in a variety of loci. The most well-known microbicide of this class is 1,3-dimethylol-5,5-dimethylhydantoin ("DMDMH"). DMDMH is generally provided as an aqueous solution, an anhyhdrous powder, or a solution in glycol. DMDMH is sold under various names, including Glydant®. These types of compounds are storage stable as supplied and do not require stabilizers to prevent chemical degradation.

STATEMENT OF THE INVENTION

The present invention is directed to stable biocidal compositions comprising at least one formaldelehyde-releasing imidazolidine, at least once 3-isothiazolone, a stabilizing amount of copper ion and solvent.

The present invention is also directed to a method of stabilizing a biocidal composition containing at least one formaldehyde-releasing imidazolidine and at least one 3-isothiazolone by the addition of a low level of copper ion.

DETAILED DESCRIPTION OF THE INVENTION

As used in this specification, the term "antimicrobial agent" refers both to a compound capable of inhibiting microbial growth (a preservative), and a compound capable of reducing microbial concentration (a disinfecting agent), within a given system. The term "antimicrobial activity" refers to the activity of the antimicrobial agents to eliminate, inhibit or prevent the growth of microorganisms. The terms "microbial organism," "microbe" and "microorganism" are used interchangeably and refer to microorganisms such as, but not limited to: fungi, bacteria, and algae. The term "locus" or "loci" refers to all industrial system or product subject to contamination by microorganisms. The following abbreviations are used throughout this specification: AI=active ingredient, nmL=milliliter; g=grams. Unless specifically identified otherwise in this specification, percentages are by weight, ranges are to be read as inclusive, and ratios are weight ratios.

The present invention is based in part on the unexpected discovery that addition of 3-isothiazolones to imidazolidine compositions results in destabilization of the imidazolidines. A further unexpected discovery is that such combinations can be stabilized using low levels of copper ion.

Any 3-isothiazolone compound is useful in the compositions of the present invention. Suitable 3)-isothiazolone compounds include, but are not limited to: 5-chloro-2-methyl-3-isothiazolone; 2-methyl-3-isothiazolone; 2-ethyl-3-isothiazolone; 5-chloro-2-ethyl-3-isothiazolone; 4,5-d ichloro-2-methyl-3-isothiazolone; 2-n-octyl-3-isothiazolonie; 4,5-dichloro-2-n-i-octyl-3-isothiazolone; 1,2-benzisothiazolone; 4,5-trimethyleiie-2-methyl-3-isothiazolone; and mixtures thereof. When mixtures of 5-chloro-2-methyl-3-isothiazolone and 2-methyl-3-isothiazolone are used, the weight ratio of 5-chloro-2-methyl-3-isothiazolone to 2-methyl-3-isothiazolone is generally 991 to 1:99, preferably 90:10 to 70:30.

The imidazolidines useful in the compositions of the present invention are any formaldehyde-releasing imidazolidines, particularly those of formula I and oligomers thereof:

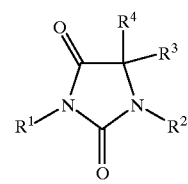

wherein:
  $R^1$ and $R^2$ are independently selected from: H; $CH_2OH$; $C_1$–$C_4$ alkyl, $C_1$–$C_4$ alkenyl or $C_1$–$C_4$ alkynyl optionally substituted with 0, S or N; provided that at least one of $R^1$ or $R^2$ is $CH_2OH$; and
  $R^3$ and $R^4$ are independently selected from: H; OH; halogen; $C_1$–$C_3$ alkoxy; $NR^5C(O)NHR^6$; $C_1$–$C_4$ alkyl, $C_1$–$C_4$ alkenyl or $C_1$–$C_4$ alkynyl optionally substituted with O, S or N; and
  $R^5$ and $R^6$ are independently selected from: H; $CH_2OH$; $C_1$–$C_4$ alkyl, $C_1$–$C_4$ alkenyl or $C_1$–$C_4$ alkynyl optionally substituted with O, S or N.

Preferred imidazolidines include diazolidinylurea, imidazolidinyl ureas and the mono- and di-methylol 5,5-dimethylhydantoins. Most preferred is 1,3-dimethylol-5,5-dimethylhydantoin.

In general, a greater amount of imidazolidine than 3-isothiazolone will be present in the compositions of the present invention. Ratios of imidazolidine to 3-isothiazolone will vary greatly depending on the particular application, but will typically be between 1:1 and 800:1. It is preferred that the imidazolidine to 3-isothiazolone ratio be between 10:1 and 400:1, and most preferably between 75:1 and A wide variety of copper salts are known in the art. Any copper salt which is sufficiently water soluble to provide the desired level of cupric ion in solution may be used. Suitable examples include, but are not limited to: copper sulfate, copper acetate, copper chloride, copper bromide, copper chlorate, copper perchlorate, copper nitrite and copper nitrate. Copper sulfate and copper nitrate are preferred. The copper salts are generally commercially available, for example, from Pfalz and Bauer (Waterbury, Conn.) and may be used without further purification.

The amount of cupric ion useful in the compositions of the present invention is typically 10 to 2500 ppm. The amount of cupric ion is preferably 10 to 1000 ppm, most preferably 10 to 100 ppm. Less cupric ion is needed where there is a lower concentration of 3-isothiazolone. As the concentration of the 3-isothiazolone is increased, proportionally more cupric ion is required to achieve the same stability. In general, the ratio of copper ion to 3-isothiazolone will be between 1:150 and 2:1. It is preferred to have a copper to 3-isothiazolone ratio between 1:75 and 1:1, and most preferably, between 1:15 and 1:5.

The solvents used in the compositions of the present invention can be water, organic solvent, or mixtures thereof. Any organic solvent is suitable as long as it is compatible with the end use and does not destabilize the antimicrobial agent. Suitable organic solvents include, but are not limited to: aliphatic and aromatic hydrocarbons, such as xylene anti mixtures of alkylbenzenes; halogenated aliphatic and aromatic hydrocarbons, such as ethylene dichloride and monochlorobenzene; alcohols, such as monohydric, dihydric, and polyhydric alcohols; aldehydes; ketones, such as acetone, methyl ethyl ketone, and methyl iso-butyl ketone; ethers; glycol ethers; glycol ether acetates; saturated and unsaturated fatty acids having at least four carbon atoms; esters, such as ethyl acetate, butyl acetate, glycol esters, and phthalate esters; and phenols. Preferred organic solvents are glycol ethers; glycol ether acetates; aliphatic and aromatic hydrocarbons; and alcohols. It is more preferred to utilize a mixture of glycol ethers or glycol ether acetates with water. Most preferred is water.

The compositions of the present invention may also include other stabilizers, such as metal nitrates, iodic acid or its salts, and various other inorganic salts and their like, which will not materially affect the performance of the combination compositions of the present invention. Other types of ingredients which can be included in the biocidal combinations of the present invention may include, without limitation: ethylenediamine tetraacetic acid, benzyl alcohol, phenoxyethanol, methyl or propyl paraben, or other biocides.

The compositions of the present invention can be used to inhibit the growth of microorganisms by introducing a microbicidally effective amount of the composition onto, into, or at a locus subject to microbial attack. Suitable loci include, but are not limited to: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics and toiletries; shampoos; soaps; detergents; surfactants; industrial disinfectants or sanitizers, such as cold sterilants, hard surface disinfectants; floor polishes; laundry rinse water; fabric softeners; metalworking fluids; conveyor lubricants; hydraulic fluids; leather and leather products; textiles; textile products; wood and wood products, such as plywood, chipboard, flakeboard, laminated beams, oriented strandboard, hard board, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; and pools and spas. Preferred loci are cosmetics and toiletries; latexes; emulsions and dispersions; paints; surfactants; floor polishes; fabric softeners; detergents; and household products.

The total amount of biocidal actives suitable to inhibit or control the growth of microorganisms will depend on the relative concentrations of imidazolidine and 3-isothiazolone, as well as the locus to be protected, but will generally be between 200 and 7000 ppm, based on the volume of said locus to be protected. It is preferred to use between 500 and 2500 ppm. It is of course within the scope of the present invention that the compositions may adlditionally include other biocidal actives.

The following examples are presented to illustrate further various aspects of the present inventioni, but are not intended to limit the scope of the invention in anv respect.

EXAMPLE 1

The following is a study of storage stability of combinations of imidazolidine and 3-isothiazolone as compared to either active alone.

Samples for the combinations were prepared as follows. DMDMH (55% AI in water) was diluted in distilled water to the appropriate concentration and thoroughly mixed. Stabilizer was added next (the amount based on the amount of $Cu^{2+}$ in $CuSO_4 \cdot 5H_2O$), and the sample mixed well. An appropriate amount of 3-isothiazolone (3:1 ratio of CMI:MI) was then melted in a small amount of hot tap water, added to the sample, and then mixed thoroughly. Other samples, i.e., not containing DMDMH, ITA or stabilizer, were prepared in analogous fashion.

After preparation, each sample was sub-sampled into approximately 10 g glass vials. The vials were then capped, the tops taped, and the vials stored at constant temperature ovens for the duration of the study. Samples were viewed weekly for any visual changes, and aliquots taken at various times during the study. AI levels were measured usinlg HPLC, and remaining percent AI levels determined using the initial measurement (Week 0) as 100% AI.

| | | | | AI Remaining | | | |
|---|---|---|---|---|---|---|---|
| | Ingredients of Composition | | | 4 Weeks @ 55° C. | | 8 Weeks @ 55° C. | |
| ID | % CMI* | % DMDMH | $Cu^{2+}$ (ppm) | % CMI | % DMDMH | % CMI | % DMDMH |
| A | 0.13 | — | — | 85 | — | 54 | — |
| B | 0.14 | — | 100 | 93 | — | 86 | — |
| C | — | 49.3 | — | — | 93 | — | 94 |

-continued

| | Ingredients of Composition | | | AI Remaining | | | |
|---|---|---|---|---|---|---|---|
| | | | | 4 Weeks @ 55° C. | | 8 Weeks @ 55° C. | |
| ID | % CMI* | % DMDMH | $Cu^{2+}$ (ppm) | % CMI | % DMDMH | % CMI | % DMDMH |
| D | — | 49.4 | 100 | — | 92 | — | 92 |
| E | 0.14 | 49.3 | — | 50 | 87 | 31 | 82 |
| F | 0.15 | 49.4 | 100 | 100 | 91 | 100 | 91 |

*The ITA used included both MI and CMI, but only the CMI level was measured.

The results clearly show that the imidazolidine alone is storage stable and does not require the addition of a stabilizer, but that when a 3-isothiazolone is added to the composition, the stability of the imidazolidine is reduced.

EXAMPLE 2

The followinlg example further demonstrates the storage stability of compositionis of the present invention. Samples were prepared in accordance with the procedures of Examples 1, above.

| | Ingredients of Composition | | | AI Remaining | | | |
|---|---|---|---|---|---|---|---|
| | | | | 4 Weeks @ 55° C. | | 12 Weeks @ 40° C. | |
| ID | % CMI* | % DMDMH | $Cu^{2+}$ (ppm) | % CMI | % DMDMH | % CMI | % DMDMH |
| G | 0.18 | 51.0 | — | 50 | 77 | 44 | 90 |
| H | 0.18 | 49.2 | 100 | 100 | 100 | 72 | 95 |
| J | 0.43 | 37.2 | — | 9 | 77 | 21 | 85 |
| K | 0.48 | 37.2 | 100 | 98 | 84 | 75 | 100 |

The results indicate that stability of both DMDMH and the 3-isothiazolones are greatly increased when copper ion is added.

What is claimed is:

1. A stable biocidal composition comprising: at least one formaldehyde-releasing imidazolidine; at least one 3-isothiazolone; a stabilizing amount of copper ion; and solvent.

2. The composition of claim 1, wherein the formaldelhyde-releasing imidazolidine is of formula I or is an oligomer thereof:

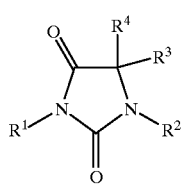

I wherein:
$R^1$ and $R^2$ are independently selected from: H; $CH_2OH$; $C_1-C_4$ alkyl, $C_1-C_4$ alkenyl or $C_1-C_4$ alkynyl optionally substituted with O, S or N; provided that at least one of $R^1$ or $R^2$ is $CH_2OH$; and
$R^3$ and $R^4$ are independently selected from: H; OH; halogen; $C_1-C_3$ alkoxy; $NR^5C(O)NHR^6$; $C_1-C_4$ alkyl, $C_1-C_4$ alkenyl or $C_1-C_4$ alkynyl optionally substituted with O, S or N; and
$R^5$ and $R^6$ are indiependently selected from: H; $CH_2OH$; $C_1-C_4$ alkyl, $C_1-C_4$ alkenyl or $C_1-C_4$ alkynyl optionally substituted with O, S or N.

3. The composition of claim 2, wherein the imidazolidinie of formula I is selected from the group consisting of: diazolidinylurea, imidazolidinyl ureas, mono-methylol 5,5-dimethylhydiantoin, and di-methylol 5,5-dimethylhydantoin.

4. The composition of claim 1, wherein the 3-isothiazolone is selected from the group consisting of: 5-chloro-2-methyl-3-isothiazolone; 2-methyl-3-isothiazolone; 2-ethyl-3-isothiazcolonie; 5-chloro-2-ethyl-3-isothiazolone; 4,5-dichloro-2-methyl-3-isothiazolone; 2-n-octyl -3-isothiazolonie; 4,5-dichloro-2-n-octyl-3-isothiazolone; 1,2-benzisothiazolone; 4,5-trimethylene-2-methyl-3-isothiazolone; and mixtures thereof.

5. The composition of claim 4, wherein the 3-isothiazolone comprises a mixture of 5-chloro-2-methyl-3-isothiazolone anti 2-methyl -3-isothiazolone.

6. The composition of claim 1, wherein the weight ratio of copper ion to 3-isothiazolone is between 1:150 and 2:1.

7. The composition of claim 1, wherein the weight ratio of said imidazolidine to 3-isothiazolonie is between 1:1 and 500:1.

8. A method of stabilizing a biocidial composition containing at least one formaldehyde-releasing imindazolidine and at least one 3-isothiazolone comprising adding an effective stabilizing amount of copper ion to a biocidal composition comprising at least one formaldehyde-releasing imidazolidine and at least one 3-isothiazolone.

9. The method of claim b8, wherein the weight ratio of copper ion to 3-isothiazolone is between 1:150 andi 2:1.

10. The method of claim 8, wherein the weight ratio of said imidiazolidine to 3-isothiazolone is between 1:1 and 500:1.

* * * * *